Figure 1:
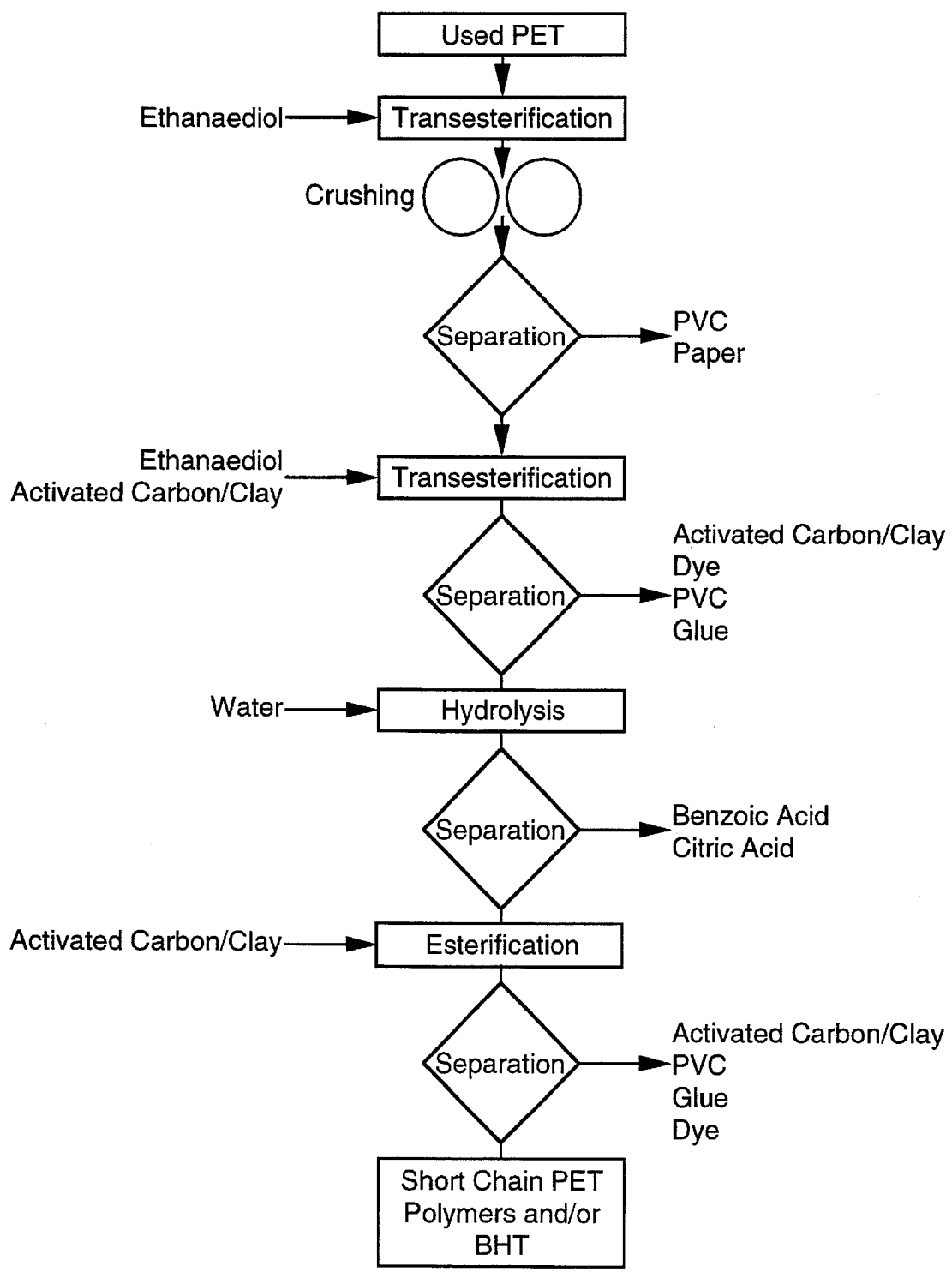

United States Patent [19]

West

[11] Patent Number: 5,504,121

[45] Date of Patent: Apr. 2, 1996

[54] POLYETHYLENE TEREPHTHALATE DECONTAMINATION

[75] Inventor: Simon M. West, Williamstown, Australia

[73] Assignee: SWIG Pty Ltd., Malvern Victoria, Australia

[21] Appl. No.: 331,669

[22] PCT Filed: May 4, 1993

[86] PCT No.: PCT/AU93/00198

§ 371 Date: Nov. 16, 1994

§ 102(e) Date: Nov. 16, 1994

[87] PCT Pub. No.: WO93/23465

PCT Pub. Date: Nov. 25, 1993

[30] Foreign Application Priority Data

May 18, 1992 [AU] Australia ................................. PL2470
Jan. 27, 1993 [AU] Australia ................................. PL9561

[51] Int. Cl.⁶ ..................................................... C08J 11/04
[52] U.S. Cl. ..................... 521/48.5; 521/40; 528/308.1; 528/308.2; 528/308.4; 528/308.6; 528/481; 528/495; 528/499; 528/503; 210/767; 210/772; 210/908
[58] Field of Search ................. 521/40, 48.5; 528/308.1, 528/308.2, 308.4, 308.6, 481, 495, 499, 503; 210/767, 772, 908

[56] References Cited

U.S. PATENT DOCUMENTS

| | | | |
|---|---|---|---|
| 3,257,335 | 6/1966 | Whitfield, Jr. et al. | 521/48.5 |
| 3,703,488 | 11/1972 | Morton | 521/48.5 |
| 3,776,945 | 12/1973 | Ligorati et al. | 560/96 |
| 3,814,786 | 6/1974 | Gull et al. | 264/542 |
| 3,884,850 | 5/1975 | Ostrowski | 521/48.5 |
| 3,907,868 | 9/1975 | Currie et al. | 560/98 |
| 4,360,661 | 11/1982 | Horlbeck et al. | 528/272 |
| 4,620,032 | 10/1986 | Doerr | 562/483 |
| 5,073,203 | 12/1991 | Al-Ghatta | 134/11 |
| 5,101,064 | 3/1992 | Dupont et al. | 560/78 |
| 5,298,530 | 3/1994 | Gamble et al. | 521/48.5 |

FOREIGN PATENT DOCUMENTS

| | | |
|---|---|---|
| 0550979 | 7/1993 | European Pat. Off. |
| 43-2088 | 1/1968 | Japan. |
| 1061542 | 3/1967 | United Kingdom. |
| 1334558 | 10/1973 | United Kingdom. |
| 2123403 | 2/1984 | United Kingdom. |
| WO93/20125 | 10/1993 | WIPO. |
| WO93/24440 | 12/1993 | WIPO. |
| WO93/24441 | 12/1993 | WIPO. |

OTHER PUBLICATIONS

Golovoy, "Hydrolysis of 1,4–Cyclohexanedimethanol––based Copolyester," *Polymer Engineering and Science*, 29(16), 1103–1106 (Aug. 1989).

Masi et al., "Tensile Behavior of High–Density Thermosetting Polyester Foams," *Polymer Engineering and Science*, 24(7), 469–472 (May 1984).

Chapter 15, "Polyester Resins (Saturated)" in *Polymer Manufacturing—Technology and Health Effects*, (Radiant Corporation, Noyes Data Corporation), 320–340 (1986).

"Polyester Fibres," pp. 64–65, 72–73, 82–84 (publication details unknown).

(List continued on next page.)

Primary Examiner—Samuel A. Acquah
Attorney, Agent, or Firm—Leydig, Voit & Mayer, Ltd.

[57] ABSTRACT

A process for removing contaminants from PET components by depolymerising poly ethylene terephthalate ("PET") comprising transesterifying material containing PET by reacting ethanediol having a temperature at or about the boiling point of ethanediol with the material for a predetermined period of time to form a solution containing soluble short chain PET polymers and/or bis (hydroxy ethyl) terephthalate ester ("BHT"); recovering short chain PET polymers and/or BHT and ethanediol; and hydrolysing the recovered short chain PET polymers and/or BHT at elevated pressure and temperature for a predetermined period of time to form an ethanediol solution and crystals of terephthalic acid.

43 Claims, 1 Drawing Sheet

OTHER PUBLICATIONS

"Scrap Recovery," pp. 167–172 (publication details unknown).

"Raw Materials Manufacture and Purification," pp. 30–36 (publication details unknown).

"Polycondensation," pp 159–162 (publication details unknown).

"Heats of Mixing," pp. 1417–1418 (publication details unknown).

"Saturated Polyesters," pp. 200–223, 356–369, 530–541 (publication details unknown).

POLYETHYLENE TEREPHTHALATE DECONTAMINATION

FIELD OF THE INVENTION

The invention relates a method for the decontamination of poly ethylene terephthalate ("PET").

BACKGROUND OF THE INVENTION

PET is a thermoplastic polyester that can be formed from 1,2-dihydroxyethane ("ethanediol") and terephthalic acid by direct esterification to form bis (hydroxy ethyl) terephthalate ester ("BHT") which is then polymerised by catalysed ester exchange to useful polymers.

Traditionally, PET has been used extensively because it can be offered as an oriented film or fibre, has high tenacity, good electrical resistance and low moisture absorption together with a melting point of approximately 265 degrees Celsius.

For these reasons, its uses have been very diverse extending from being blended with cotton for wash and wear fabrics, blended with wool for worsteds and suitings, packaging films and recording tapes and containers including soft drink containers.

There are a number of applications of PET where remelting and reforming is not permissible or gives inferior properties. The reuse of PET for these applications is best achieved by degrading the polymer into the original monomers namely ethanediol and terephthalic acid then reacting the monomers together to regenerate the original PET.

The known art (British Patent No. 610135) is to hydrolyse PET with either strong alkalis or acids. The alkalis must be neutralised with acid to produce terephthalic acid resulting in a significant cost of reagents and possible contamination of the product with alkali metal ions. The strong acids must be recovered and the ethanediol separated. Further the acids dissolve paper and pigments to give by products which are difficult to separate.

It is known that PET will transesterify with ethanediol (British Patent No. 610136) but the product BHT, is not a convenient intermediate for subsequent purification to remove esters of contaminant acids such as benzoic and adipic acid.

Accordingly, the present invention is directed to an improved process of decontaminating PET.

DESCRIPTION OF THE INVENTION

Accordingly, in one form of this invention, there is provided a process for removing contaminants from PET components by depolymerising PET comprising the following steps:

(a) transesterifying material containing PET by reacting ethanediol having a temperature at or about the boiling point of ethanediol with the material for a predetermined period of time to form a solution containing soluble short chain PET polymers and/or BHT;

(b) recovering short chain PET polymers and/or BHT and ethanediol; and (c) hydrolysing the recovered short chain PET polymers and/or BHT at elevated pressure and temperature for a predetermined period of time to form an ethanediol solution and crystals of terephthalic acid.

According to another form of the invention, there is provided a process for removing contaminants from PET components by depolymerising PET comprising the following steps:

(a) transesterifying material containing PET by mixing ethanediol having a temperature at or about the boiling point of ethanediol with the material for a predetermined period of time to form mixture containing embrittled PET;

(b) crushing the mixture and separating uncrushed material from the crushed material which contains PET;

(c) transesterifying the, PET by reacting ethanediol having a temperature at or about the boiling point of ethanediol, with the recovered PET for a predetermined period of time to form a solution containing soluble short chain PET polymers and/or BHT;

(d) recovering short chain PET polymers and/or BHT and ethanediol; and (e) hydrolysing the recovered short chain PET polymers and/or BHT at elevated pressure and temperature for a predetermined period of time to form an ethanediol solution and crystals of terephthalic acid.

According to yet another form of the invention, there is provided a process for removing contaminants from PET components by depolymerising PET comprising the following steps:

(a) transesterifying the material containing PET by mixing ethanediol having a temperature at or about the boiling point of ethanediol with the material for a predetermined period of time to form a mixture containing embrittled PET;

(b) crushing the mixture and separating uncrushed material from the crushed material containing PET;

(c) hydrolysing the PET in the mixture at elevated pressure and temperature for a predetermined period of time to form an ethanediol solution and crystals of terephthalic acid;

(d) esterifying the ethanediol solution and crystals of terephthalic acid to form short chain PET polymers and/or BHT; and (e) recovering short chain PET polymers and/or BHT from the mixture.

It has been surprisingly found that ethanediol at or near its boiling point reacts with PET but does not react significantly with products often used in PET containing products including paper, other plastics (for example, poly vinyl chloride ("PVC"), colouring dyes, pigments, mineral sands or clays ("Contaminants").

Typically the step or steps involving transesterification with ethanediol are carried out at a temperature of within 10 degrees Celsius of the boiling point of ethanediol and more preferably at a temperature of within 5 degrees Celsius of the boiling point of ethanediol. Such temperature fluctuations do not substantially affect the lack of reactivity of the ethanediol with the Contaminants.

Transesterification of PET with ethanediol according to the invention can result in the PET either becoming embrittled or solubilising depending on the period of time over which the transesterification is allowed to take place. At the various stages, separation of the PET containing mixtures or solutions can be affected by known separation techniques.

Preferably, embrittlement is caused to occur after a period of between between 20 minutes and 60 minutes and more preferably between 30 minutes and 50 minutes.

In the case of solubilisation, the transesterification takes place over a preferred period of at least one or two hours and even more preferably about two hours. PET will solubilise after longer periods of transesterification because of the solubility of short chain PET polymers and/or BHT in ethanediol. If all or a substantial portion or the PET is transesterified to BHT which raises the boiling point of the solution, the reaction time may be less because the higher boiling temperature will drive the reaction more quickly.

Embrittlement which takes place prior to the collapse of the original PET structure allows the PET to be crushed to separate it from Contaminants. This allows separation to take place on the basis of size and density. Crushing to less than 1 millimeter is preferred. Crushing can be achieved by rollers or hammer mills or any other known technique for reducing the size of particles. Once crushed, the PET is separated from typical Contaminants such as hydrocarbons and pigments from paper. Other substances giving rise to coloured products can be separated by screening, washing or density separation from other Contaminants which have not become embrittled or have solubilised in the ethanediol such as paper fragments in ethanediol or pulp in water medium.

Once solubilised, separation of the PET rich fraction in one form of the invention can take place preferably by filtration methods and more preferably by high pressure filtration methods. The addition of activated carbon or a combination or activated carbon and activated clay is used as an adsorbant for a wide variety of molecules such as dyes, pesticides, coloured polymers, etc.

Other foreign plastics with an alkane chain do not depolymerise in the boiling ethanediol but only melt so that they may be removed by either flotation on the denser ethanediol (1114 kilograms/m$^3$), screened or filtered from embrittled PET or the short chain PET polymer and/or BHT solution. Proteins and polyamides do not react with ethanediol and are recovered with the other plastics. Other polyesters are also transesterified and contaminate the short chain PET polymer solution. It can be understood that this present invention does not claim that all the PET is converted to BHT only that the polymer chain length is short so that the terephthalate containing molecules are soluble in hot ethanediol to permit separation of foreign materials and rapid subsequent hydrolysis.

Following transesterification, the short chain PET polymers and/or BHT can be purified by crystallisation in water liberating excess ethanediol. The precipitate is filtered off. The filtrate containing ethanediol is recovered by fractional distillation from the additional water (British Patent No 610136). Water soluble impurities such as sugar and citric acid from soft drinks are partially removed in the filtrate and rejected as an involatile residue by distilling off the ethanediol.

Although it will be understood that the proportions of ethanediol to PET is not critical to the transesterification of the PET, TNT preferred forms of the invention the proportion of ethanediol to PET is at least 1:1. Excess ethanediol can be recovered by distillation techniques well known to those skilled in the art.

The short chain PET polymers and/or BHT are hydrolysed with water at elevated pressures and temperatures to give ethanediol and crystalline terephthalic acid. Typically, hydrolysis is achieved by dispersing the short chain PET polymers and/or BHT in a water slurry in a high pressure vessel and heating it to more than 180 degrees Celsius for 2 hours and then allowing it to cool. This treatment gives good hydrolysis without the requirement for catalysts (which contaminate the product) and also gives good crystals of terephthalic acid with a high purity due to the greatly increased solubility at the higher temperature. The crystals are washed with water to remove ethanediol which is recovered as described before.

A number of water soluble substances (for example, citric acid, phosphoric acid, sodium chloride and sulphuric acid) in the feed stock will be present in the mixture of terephthalic acid and ethanediol and are separated by the filtration. Additionally, a wide variety of compounds such as protein, paper, fats and some pesticides will be hydrolysed and made water soluble relative to the very insoluble terephthalic acid.

Contamination of the short chain PET polymers and/or BHT by benzoic, adipic and sebacic acid is rectified because the free acids are approximately 1000 times more soluble in the wash water allowing some foreign polyester in the feed.

The hydrolysis can be improved by using a reactor of annular format where heating is followed by partial cooling to allow the solubility of terephthalic acid to cycle and assist crystallisation and removal from the aqueous phase. Further improvement in hydrolysis Is given by allowing some boiling of the hydrolysing mixture then condensing and removing an ethanediol rich phase. The contaminant water soluble substances can be removed either prior to the transesterification by water washing and drying or after hydrolysis in the water and ethanediol solution and then are rejected in the residue after distillation of the water and ethanediol.

The ethanediol is readily purified by distillation and may be partially recycled to give both product for further polymerisation and enough product to react with fresh PET. Contaminant alcohols such as methanol from ethylene methyl acrylate or hexanediol from polyester are separated in the distillation step.

DESCRIPTION OF THE DIAGRAM

One form of the invention is illustrated in the flow chart.

Used PET is initially subjected to transesterification with boiling ethanediol for sufficient time to embrittle PET. Thereafter the mixture is passed through rollers which crush embrittled PET.

The non-crushed (ductile) components of the mixture are separated by screening from the remainder of the mixture. The PET fines are then subjected to a further transesterification process.

Activated carbon and clay is added during transesterification to adsorb contaminants. During this further transesterification process the PET is converted into short chain PET polymers and/or BHT which are soluble.

The resultant solution is subjected to a further separation by screening and/or high pressure filtration to remove contaminants such as activated carbon, clay, dye, PVC and glue.

The filtrate is hydrolysed with very pure water under elevated pressures and temperatures to form ethanediol and crystalline terephthalic acid. Acids (for example, benzoic and citric acid) remain in solution and are separated from crystalline terephthalic acid.

The ethanediol and terephthalic acid are esterified to short chain PET polymers and/or BHT. Activated carbon and activated clay are added and then any remaining contaminants for example PVC, glue and dye are removed by filtration.

EXAMPLES

The invention is illustrated by the following non-limiting examples.

Example 1

PET bottles of mixed colour were dissected to give 500 grams of fragments which were transferred to a flask with a reflux condenser. 500 grams of ethanediol was added and then the apparatus was heated to boil the ethanediol with reflux until the PET was solubilised (approximately 2 hours) and a further 30 minutes to increase the conversion to short chain PET polymers and/or BHT. The paper and polyethylene fragments were screened off then the coloured solution was treated with 1 gram of activated carbon for 5 minutes and filtered. The filtrate was added to 1 liter of boiling water with mixing then allowed to cool to give a precipitate of short chain PET polymers and/or BHT which is filtered off. The filtrate was retained for ethanediol recovery. The short chain PET polymers and/or BHT was dispersed in an equal weight of water and transferred to a pressure vessel then heated at 200 degrees Celsius for 2 hours then allowed to slowly cool.

The mass was filtered to give crystalline terephthalic acid and the filtrate retained. The two filtrates were combined and fractionally distilled to separate the ethanediol from water and involatiles.

Example 2

25 gram samples of the following plastics were heated in 200 grams of boiling ethanediol for 2 hours then the plastic recovered:

Low density polyethylene, High density polyethylene, Polypropylene, Ethylene methyl acrylate-ethylene copolymer 2205, Ethylene butyl acrylate-ethylene copolymer DFDS 6430 and Ethylene-vinyl acetate copolymer 28–800. In each case the plastic melted but was otherwise unaffected and was readily recovered from the solvent.

Example 3

1 kilogram of ethanediol was heated to 190 degrees Celsius then 600 grams of granulated PET soft drink bottle was added and heated for 45 minutes. The solid PET was screened off then crushed between rolls to particles less than 1 millimeter, while paper label passed through the rolls unaffected. The crushed PET was divided into equal parts which were treated separately. One part was screened using ethanediol as an aid then the fines passing the screen were heated for one hour to convert the PET to soluble products. A mixture of 5 grams activated carbon and 5 grams of activated clay were added and the mixture heated and stirred for 15 minutes then filtered and the product hydrolysed to give short chain PET polymers and/or BHT and ethanediol. The second part was screened with water then the product PET purified by washing with hindered settling to remove fine paper fibres and small particles. The product was dried and treated as above.

Example 4

A reactor was constructed from 3 meters of 21 millimeter pipe and a 1 liter bowl as an annulus with the plane of the ring held vertical. 1.5 liters of water was added to the reactor and the temperature brought to 200 degrees Celsius then a molten mixture of 100 grams of short chain PET polymers and/or BHT and 100 grams of ethanediol added to the water and maintained at 200 degrees Celsius for two hours by heating one segment of the annulus and allowing the rest to be partially cooled by the atmosphere. The apparatus was then cooled and crystalline terephthalic acid and ethanediol recovered from the water suspension.

Example 5

A sample of terephthalic acid (100 grams) was taken and dispersed in 1 liter of ethanediol and heated at the boiling point with reflux to remove water of reaction for 4 hours. A mixture of 2 grams of activated carbon and 2 grams of activated clay was added and stirred for 30 minutes then filtered off to remove PVC, PET dyes ere and then the excess ethanediol was distilled off and the polymerisation was completed by heating to 270 degrees Celsius under vacuum to produce a PET polymer.

The process described above can be used to effectively treat a variety of materials which con thin PET to give pure monomers for repolymerisation. This discovery allows the use of dirty whole bottles with unsorted foreign plastics and attached labels and tops with some foreign bottles and plastic debris. The process can also be used to recover PET monomers from used X-ray film or mixed fabrics.

Since modifications to the steps described are various and obvious to those skilled in this art it is to be understood that this invention is not limited to the particular embodiments described.

I claim:

1. A process for removing contaminants from PET components by depolymerising poly ethylene terephthalate ("PET") comprising the following steps:

(a) transesterifying material containing PET by reacting ethanediol having a temperature at or about the boiling point of ethanediol with the material for a predetermined period of time to form a solution containing soluble short chain PET polymers and/or his (hydroxy ethyl) terephthalate ester ("BHT");

(b) recovering short chain PET polymers and/or BHT and ethanediol; and (c) hydrolysing the recovered short chain PET polymers and/or BHT at elevated pressure and temperature for a predetermined period of time to form an ethanediol solution and crystals of terephthalic acid.

2. The process of claim 1, wherein step (a) is carried out at temperature of within 10 degrees Celsius of the boiling point ethanediol.

3. The process of claim 1, wherein step (a) is carried out at a temperature of within 5 degrees Celsius of the boiling point of ethanediol.

4. The process of claim 1, wherein the proportion of ethanediol to PET is at least 1:1.

5. The process of claim 1, wherein the predetermined period of time in step (a) is at least one hour.

6. The process of claim 1, wherein the predetermined period of time in step (a) is at least two hours.

7. The process of claim 1, wherein the predetermined period of time in step (a) is about two hours.

8. The process of claim 1, wherein the PET and ethanediol are recovered in step (b) by filtration.

9. The process of claim 8, wherein the filtration is high pressure filtration.

10. The process according to claim 9, wherein the filtration includes the addition off activated carbon or a combination of activated carbon and activated clay.

11. A process for removing contaminants from PET components by depolymerising poly ethylene terephthalate ("PET") comprising the following steps:

(a) transesterifying material containing PET by mixing ethanediol having a temperature at or about the boiling point of ethanediol with the material for a predetermined period of time to form a mixture containing embrittled PET;

(b) crushing the mixture and separating uncrushed material from the crushed material which contains PET;

(c) transesterifying the PET by reacting ethanediol having a temperature at or about the boiling point of ethanediol with the recovered PET for a predetermined period of time to form a solution containing soluble short chain PET polymers and/or his (hydroxy ethyl) terephthalate ester ("BHT");

(d) recovering short chain PET polymers and/or BHT and ethanediol; and (e) hydrolysing the recovered short chain PET polymers and/or BHT at elevated pressure aria temperature for a predetermined period of time to form an ethanediol solution and crystals of terephthalic acid.

12. The process of claim 11, wherein step (a) is carried out at a temperature of within 10 degrees Celsius of the boiling point of ethanediol.

13. The process of claim 11, wherein step (a) is carried out at a temperature of within 5 degrees Celsius of the boiling point of ethanediol.

14. The process of claim 11, wherein the proportion of ethanediol to PET in step (a) is at least 1:1.

15. The process of claim 11, wherein the predetermined period of time in step (a) is between 20 minutes and 60 minutes.

16. The process of claim 11, wherein the predetermined period of time in step (a) is between 30 minutes and 50 minutes.

17. The process of claim 11, wherein the PET is crushed to a size of less than 1 millimeter.

18. The process of claim 11, wherein step (c) is carried out at a temperature of within 10 degrees Celsius of the boiling point of ethanediol.

19. The process of claim 11, wherein step (c) is carried out at a temperature of within 5 degress Celsius of the boiling point of ethanediol.

20. The process of claim 11, wherein the proportion of ethanediol to PET in step (c) is at least 1:1.

21. The process of claim 11, wherein the predetermined period of time in step (c) is at least one hour.

22. The process of claim 11, wherein the predetermined period of time in step (c) is at least two hours.

23. The process of claim 11, wherein the predetermined period of time in step (c) is about two hours.

24. The process of claim 11, wherein the PET and ethanediol are recovered in step (d) by filtration.

25. The process of claim 24, wherein the filtration is high pressure filtration.

26. The process according to claim 25, wherein the filtration includes the addition of activated carbon or a combination of activated carbon and activated clay.

27. The process of claim 11, wherein step (b) includes the step of density separation.

28. A process for removing contaminants from poly ethylene terephthalate ("PET") components comprising the following step:

(a) transesterifying the material containing PET by mixing ethanediol having a temperature at or about the boiling point of ethanediol with the material for a predetermined period of time to form a mixture containing embrittled PET;

(b) crushing the mixture and separating uncrushed material from the crushed material containing PET;

(c) hydrolysing the PET in the mixture at elevated pressure and temperature for a predetermined period of time to form an ethanediol solution and crystals of terephthalic acid;

(d) esterifying the ethanediol solution and crystals of terephthalic acid to form short chain PET polymers and/or his (hydroxy ethyl) terephthalate ester ("BHT"); and (e) recovering short chain PET polymers and/or BHT from the mixture.

29. The process of claim 28, wherein step (a) is carried out at a temperature of within 10 degrees Celsius of the boiling point of ethanediol.

30. The process of claim 28, wherein step (a) is carried out at temperature of within 5 degrees Celsius of the boiling point ethanediol.

31. The process of claim 28, wherein the proportion of ethanediol to PET in step (a) is at least 1:1.

32. The process of claim 28, wherein the predetermined period of time in step (a) is between 20 minutes and 60 minutes.

33. The process of claim 28, wherein the predetermined period of time in step (a) is between 30 minutes and 50 minutes.

34. The process of claim 28, wherein the PET is crushed to a size of 1 millimeter.

35. The process of claim 28, wherein the PET and ethanediol are recovered in step (e) by filtration.

36. The process of claim 35, wherein the filtration is high pressure filtration.

37. The process according to claim 36, wherein the filtration includes the addition of activated carbon or a combination of activated carbon and activated clay.

38. A process for recycling poly ethylene terephthalate ("PET") from sources of used PET comprising the steps of claim 1.

39. A process for recycling poly ethylene terephthalate ("PET") containing diols other than ethanediol comprising the steps of claim 1.

40. A process for recycling poly ethylene terephthalate ("PET") from sources of used PET comprising the steps of claim 11.

41. A process for recycling poly ethylene terephthalate ("PET") from sources of used PET comprising the steps of claim 28.

42. A process for recycling poly ethylene terephthalate ("PET") containing diols other than ethanediol comprising the steps of claim 11.

43. A process for recycling poly ethylene terephthalate ("PET") containing diols other than ethanediol comprising the steps of claim 28.

* * * * *

UNITED STATES PATENT AND TRADEMARK OFFICE
CERTIFICATE OF CORRECTION

PATENT NO.  : 5,504,121
DATED       : April 2, 1996
INVENTOR(S) : West, Simon M.

It is certified that error appears in the above-identified patent and that said Letters Patent is hereby corrected as shown below:

Column 2, lines 12 and 14, "the, PET" should read
--the PET- and "ethanediol, with" should read
--ethanediol with--.

Column 3, line 52, "TNT preferred" should read
--in preferred--.

Column 6, line 8, "con thin" should read --contain--.

Signed and Sealed this

Seventeenth Day of December, 1996

Attest:

BRUCE LEHMAN

Attesting Officer

Commissioner of Patents and Trademarks